United States Patent
Arsalan et al.

(10) Patent No.: US 10,648,841 B1
(45) Date of Patent: May 12, 2020

(54) MULTIPHASE FLOW METER COMBINING EXTENDED THROAT VENTURI WITH MICROWAVE RESONATORS

(71) Applicants: Saudi Arabian Oil Company, Dhahran (SA); King Abdullah University of Science and Technology, Thuwal (SA)

(72) Inventors: Muhammad Arsalan, Dhahran (SA); Muhammad Akram Karimi, Thuwal (SA); Atif Shamim, Thuwal (SA)

(73) Assignees: Saudi Arabian Oil Company, Dhahran (SA); King Abdullah University of Science and Technology, Thuwal (SA)

( * ) Notice: Subject to any disclaimer, the term of this patent is extended or adjusted under 35 U.S.C. 154(b) by 0 days.

(21) Appl. No.: 16/296,926

(22) Filed: Mar. 8, 2019

(51) Int. Cl.
- *G01F 1/44* (2006.01)
- *G01F 1/36* (2006.01)
- *G01F 1/58* (2006.01)
- *G01F 1/74* (2006.01)
- *G01N 22/04* (2006.01)
- *G01N 33/28* (2006.01)

(52) U.S. Cl.
CPC ............ *G01F 1/44* (2013.01); *G01F 1/363* (2013.01); *G01F 1/58* (2013.01); *G01F 1/74* (2013.01); *G01N 22/04* (2013.01); *G01N 33/2847* (2013.01)

(58) Field of Classification Search
CPC ..... G01F 1/44; G01F 1/36; G01F 1/58; G01F 1/74
See application file for complete search history.

(56) References Cited

U.S. PATENT DOCUMENTS

| | | | |
|---|---|---|---|
| 4,516,434 A | 5/1985 | Halmi | |
| 4,902,961 A | 2/1990 | De et al. | |
| 5,461,930 A | 10/1995 | Farchi et al. | |
| 5,597,961 A | 1/1997 | Marrelli | |
| 6,378,380 B1 | 4/2002 | Kusters et al. | |
| 6,612,187 B1 | 9/2003 | Lund | |
| 6,622,574 B2 | 9/2003 | Fincke | |
| 6,698,297 B2 * | 3/2004 | Gysling | G01F 1/44 |
| | | | 73/861.63 |
| 6,915,707 B2 | 7/2005 | Nyfors et al. | |
| 6,935,189 B2 | 8/2005 | Richards | |
| 7,107,860 B2 | 9/2006 | Jones | |

(Continued)

OTHER PUBLICATIONS

Ding, Feng et al.; CFD Simulation of Two-Phase Flow in a Downhole Venture Meter; Applied Mechanics and Materials, vols. 130-134, pp. 3644-3647.

(Continued)

*Primary Examiner* — Jewel V Dowtin
(74) *Attorney, Agent, or Firm* — Bracewell LLP; Constance G Rhebergen; Ryan B. McBeth (57) ABSTRACT

Embodiments of the present disclosure aim to provide advanced multiphase flow meters utilizing advanced sensor configurations and data analysis. In an embodiment, a system is provided and configured with permittivity sensors configured around the throat section of an extended throat venturi enclosure. In a particular embodiment, the permittivity sensors in the described system are configured with a computer system or a micro-computer system, that can be configured with a computer circuit board comprising a processor, memory, networking capability, and software.

18 Claims, 6 Drawing Sheets

(56) References Cited

U.S. PATENT DOCUMENTS

| | | | |
|---|---|---|---|
| 7,908,930 B2 | 3/2011 | Xie et al. | |
| 8,224,588 B2 * | 7/2012 | Wee | G01F 1/66 |
| | | | 702/30 |
| 8,322,228 B2 | 12/2012 | Xie et al. | |
| 9,002,650 B2 * | 4/2015 | Lievois | G01F 1/44 |
| | | | 250/269.1 |
| 9,528,869 B2 | 12/2016 | Xie et al. | |
| 9,624,768 B2 | 4/2017 | Yang | |
| 9,804,105 B2 | 10/2017 | Karimi et al. | |
| 9,927,270 B2 | 3/2018 | Xie et al. | |
| 2016/0131601 A1 | 5/2016 | Sharma et al. | |
| 2017/0350830 A1 | 8/2017 | Karimi et al. | |
| 2018/0011033 A1 | 1/2018 | Karimi et al. | |
| 2019/0162568 A1 * | 5/2019 | Ligneul | G01F 1/44 |

OTHER PUBLICATIONS

Elobeide, Mujahid O. et al.; Effect of inclination and water cut on venturi pressure drop measurements for oil-water flow experiments; Journal of Petroleum Science and Engineering, 147 (2016); pp. 636-646.

Fincke, J.R.; Performance characteristics of an Extended Throat Flow Nozzle for the Measurement of High Void Fraction Multi-Phase Flows; Idaho National Engineering and Environmental Laboratory, 4th International Symposium Fluid Flow Measurement; Jun. 28, 1999-Jun. 30, 1999.

Li, Xia, et al.; Oil-Water Two-Phase Flow Measurement Using a Venturi Meter And An Oval Gear Flow Meter; Chemical Engineering Communications, 197:2, 223-231, DOI:10.1080/00986440902938469.

Si, Huang, et al. Theoretical and Experimental Study on Oil-Water Two-Phase Flow in a Downhole Venturi Meter, Applied Mechanics and Materials, vol. 232, pp. 284-287.

* cited by examiner

MULTIPHASE FLOW METER COMBINING EXTENDED THROAT VENTURI WITH MICROWAVE RESONATORS

FIELD

Embodiments of the present disclosure relate to multiphase flow meters that utilize sensors and sensor data analysis to interpret complex flows.

RELATED APPLICATIONS

This application is related to and incorporates by reference U.S. Pat. No. 9,804,105 and U.S. patent application Ser. Nos. 15/686,738 and 15/686,747.

BACKGROUND

Multiphase flow meters have been configured with several sensors to gather data regarding complex flows, usually consisting of oil, water and gas. Flow meters can be further configured with computer systems or micro-computer systems to log and interpret the sensor data using math algorithms. Sensors can be utilized to detect and measure data regarding solids as well. Sensors can be combined and configured in conjunction with a venturi flow passage to enable the measurement measure mass flow and can be further configured with a method to estimate fluid fractions. For systems that can perform fluid fraction estimations several measurement sensors and technologies can be configured as part of the system. These sensors and technologies can include the followings sensors and sources, for example, radioactive, x-ray, infrared, resistivity, capacitance, and acoustic. Systems configured with these technologies have several known issues that would be desirable to address or minimize, certain methods and systems can be unsafe for handling, inaccurate, or do not perform in certain conditions.

Prior systems that have utilized extended throat venturi configurations recognize that a stabilized mixture of oil, water and gas cannot be formed when the void fraction increases to 90-95% or greater. An extended throat venturi configuration has a longer throat section than a standard venturi configuration but is otherwise similar to a standard venturi configuration. Void fraction is the fraction of gas in liquid. For example; a void fraction of 90% means that 90% of the total volume of conduit is occupied by gas phase while the rest of 10% is covered by liquid phase. When the void fraction is 90-95% or greater, interaction between gas and liquid becomes a complicated phenomenon to accurately measure. Additional pressure drops can be experienced by the gas phase due to the irreversible work done by the gas phase in accelerating the liquid phase. These pressure drops over the convergent section of the venturi can result in over-estimation (resulting into measurement error) in measuring the gas flow rates.

SUMMARY

Embodiments of the present disclosure aim to provide advanced multiphase flow meters utilizing advanced sensor configurations and data analysis.

It would be desirable to provide a system that combines electric permittivity-based water fraction measurement and mass flow measurement using extended throat venturi. Embodiments of such a system are described in the paragraphs below and can result in accurate water cut measurements over a full range (0-100%) for a configured multiphase flow meter.

According to an embodiment, a system is provided and configured with permittivity sensors configured around the throat section of an extended throat venturi enclosure. In a particular embodiment, the permittivity sensors in the described system are configured with a computer system or a micro-computer system. The computer system or micro-computer system can be further configured with a computer circuit board including a processor, memory, networking capability, and software (collectively the computer or micro-computer system). The software can include an operating system and communications interface program. In an embodiment, the configured permittivity sensors can include microwave resonators. The microwave resonators can be configured to communicate with a computer system. In an embodiment, the computer system can be configured to be located near the sensors or in an alternate embodiment the computer can be configured at a location that is remotely located. In an embodiment, the computer system can be configured to control the microwave resonators and also to receive sensor measurement data from the resonators. The computer system can be programmed to interpret, process, and analyze the sensor measurement data. In an embodiment, the system can further be configured to calculate and provide water cut analysis as well as flow rate information and other information for logging purposes, to another computer system, or to an end user.

BRIEF DESCRIPTION OF THE DRAWINGS

The foregoing aspects, features, and advantages of embodiments of the present disclosure will further be appreciated when considered with reference to the following description of embodiments and accompanying drawings. In describing embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

DETAILED DESCRIPTION

Advantages and features of the present disclosure and methods of accomplishing the same will be apparent by referring to embodiments described below in detail in connection with the accompanying drawings. The disclosed embodiments and configurations are not limited to the embodiments disclosed below and may be implemented in various different forms. The embodiments are provided only for completing the disclosure and for fully representing the scope of the disclosure to those skilled in the art.

For simplicity and clarity of illustration, the drawing figures illustrate the general manner of construction, and descriptions and details of well-known features and techniques may be omitted to avoid unnecessarily obscuring the discussion of the described embodiments. Additionally, elements in the drawing figures are not necessarily drawn to scale. For example, the dimensions of some of the elements in the figures may be exaggerated relative to other elements to help improve understanding of the various example embodiments Various embodiments will be described in detail with reference to the accompanying drawings.

Figure 1:
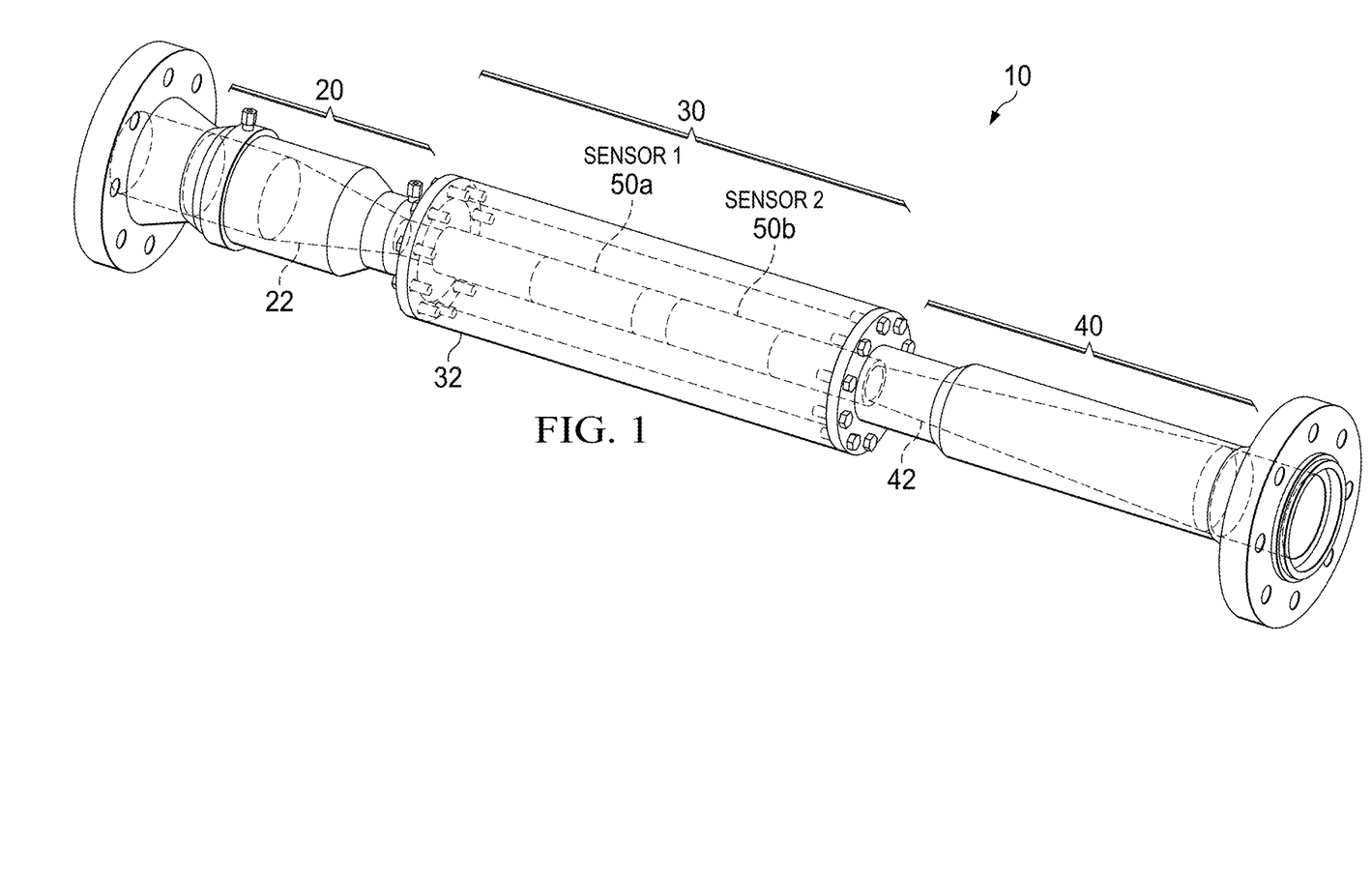
FIG. 1 illustrates a side perspective view of an example multiphase flow meter system combining an extended throat venturi with microwave resonators configured in one possible arrangement and configuration.

Embodiments of the present disclosure aim to provide advanced multiphase flow meter systems utilizing advanced sensor configurations and data analysis. According to an embodiment, and as illustrated in reference to FIG. 1, an extended throat venturi multiphase flow meter system 10 is shown. FIG. 1. illustrates an example layout of a particular system 10 having a venturi convergence section 20, an extended throat section 30, a venturi throat outer housing 32, a venturi divergence section 40, and a pair of microwave resonator sensors 50a and 50b (labeled in FIG. 1 as sensor 1 and sensor 2, respectively). In the embodiment illustrated in FIG. 1, the venturi convergence section 20 includes a convergence conical tapered section 22 that connects to the extended throat section 30. Further, the venturi divergence section 40 further includes a divergence conical tapered section 42 that extends from the extended throat section 30. In an embodiment, the taper angle of each of the convergence conical tapered section 22 and the divergence conical tapered section 42 can be the same or may differ. In an embodiment, the conical tapered section 22 can be configured as per the International Organization for Standardization or "ISO" standard 5167-4, such as is illustrated in FIG. 1. In alternative embodiments, these angles can be changed, for example, they can be increased to reduce the overall length of the meter for a given configuration such that the fluid flow passing through it can have generally smooth and non-turbulent flow. Each of these features, may be configured differently or organized differently for a particular system. As such, the layout of FIG. 1, should be viewed as merely one example since each system may have a unique layout and configuration.

Figure 5:
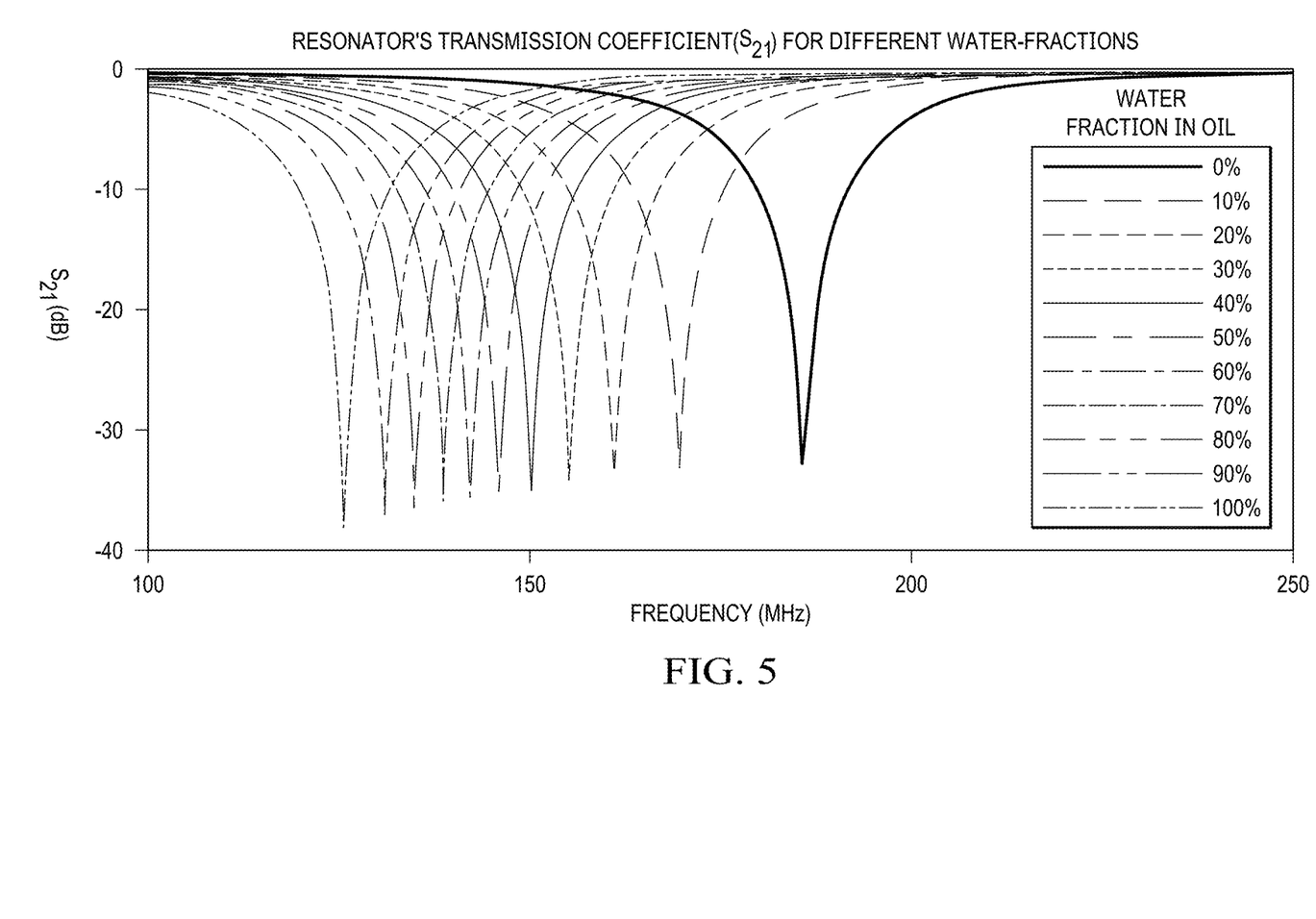
FIG. 5 illustrates one possible outcome of simulation results for a resonator's response to different water fractions from 0-100% for the system and configuration illustrated and described with respect to FIG. 4.

Referring to FIG. 1, in an embodiment, an extended throat venturi multiphase flow meter system 10 utilizes the extended throat 30 as the section on which to configure the pipe conformable microwave resonator sensors 50a and 50b. The time-based response of these two sensors is analyzed to estimate the water-cut of the fluid passing through the pipe section. In an embodiment, to extract water-cut measurements, both resonator sensor 50a and resonator sensor 50b are excited by microwave signals followed by recording their responses. This results in a plurality of time-based S parameter measurements typical of microwave resonators and similar to those shown in FIG. 5 (FIG. 5 is described in more detail in the paragraphs below) on the $S_{21}$ (decibel or "dB") axis of the graph shown in FIG. 5. The dip point (minimum magnitude) can then be extracted from the curve established by the logged sensor measurements and the corresponding frequency at that minimum or "min." point is determined as resonance frequency ($f_o$) of the sensor. The determined $f_o$ of each of the two sensors is averaged to get the averaged $f_o$, which is solely dependent on water content in oil and is independent of the flow regime/pattern inside the conduit. These measurements can be done either using vector network analyzers ("VNAs") or microwave oscillators. An example embodiment using VNAs is shown and described with respect to FIG. 6. The process is repeated every 100 milliseconds or "msec" so that the dynamics of the change in fluid flow can be captured. The capability to do 100 msec time based measurements further allows for the determination of water-fraction content in the presence of 3-phases (oil, water and gas), and further allows for the prediction of flow patterns of the fluid passing through the conduit. Moreover, the time-based response of these two sensors can also be correlated to extract the flow rate or can be used to estimate the void fraction. Void fraction is the fraction of gas in liquid. In an embodiment, the two resonators have a certain known distance between them. This allows the time-based response ($f_o$) of two resonators to be correlated and the maximum correlation value relates to the delay between the responses of two resonators. The known distance between the resonators is then divided by the time delay to give the flow rate of the fluid.

The convergence section of the venturi is configured to measure the differential pressure such that the flow rate of the mixture can be determined. In addition, more pressure points may be tapped for measurement on the extended throat to allow for extracting the flow rate of the gas phase in addition to the liquid phases. This provides another method to measure the flow rate in addition to the correlation method mentioned above. In an embodiment, the correlation method, the differential pressure method, or both, can be configured to measure flow rate depending on the desired configuration of a particular system.

In general, an extended throat venturi system, such as those described, can be configured according to the following calculations and metrics. For example, when a microwave resonator is configured at the throat of an extended throat venturi, the venturi measures the mass flow from the following equation:

$$\dot{m} = \rho V A$$

Where:
$\dot{m}$ = Mass Flow Rate
$\rho$ = Fluid Density
V = Fluid Velocity
A = Cross sectional flow area As a further example, if fluid density is known then the following equation can be used to determine the volumetric flow rate:

$$Q = C_D \frac{\pi d^2}{4} \frac{\varepsilon}{\sqrt{1-\beta^4}} \sqrt{\frac{2\Delta P}{\rho_{mix}}}$$

Where:
 Q = Volumetric Flow Rate
 $C_D$ = Discharge coefficient
 d = Throat diameter
 β = d/D: Diameter ratio of throat (d) to the upstream pipe (D).
 ε = Compressibility factor
 ΔP = Differential pressure across the Venturi
 $\rho_{mix}$ = Effective density of the two-phase mixture In an example, phase fractions can then be determined by the following equation:

$$\rho_{mix} = \alpha_w \rho_w + \alpha_o \rho_o$$

Where:
 $\rho_{mix}$ = Effective density of the two-phase mixture
 $\alpha_w$ = Water fraction
 $\rho_w$ = Water density
 $\alpha_o$ = Oil fraction
 $\rho_o$ = Oil density In an embodiment, the microwave resonators in a particular system can be configured to have greater sensitivity to the water-cut in the flow than previous systems. The water and oil fraction ($\alpha_w$, and $\alpha_o$) can be determined from the multiphase flow going through extended throat of the venturi by correlating the change in resonance frequency. The water and oil densities ($\rho_w$, and $\rho_o$) from a specific reservoir can be determined by taking samples. The density of the mixture $\rho_{mix}$ can be obtained using the calculated fractions and densities. The volumetric flow rate can be determined with $\rho_{mix}$ using the Q equation above. As both oil and water are incompressible fluids in normal filed conditions, the individual volume and mass flow rates can be obtained by multiplying the total flow rate with the individual fractions ($\alpha_w$, and $\alpha_o$).

Figure 2:
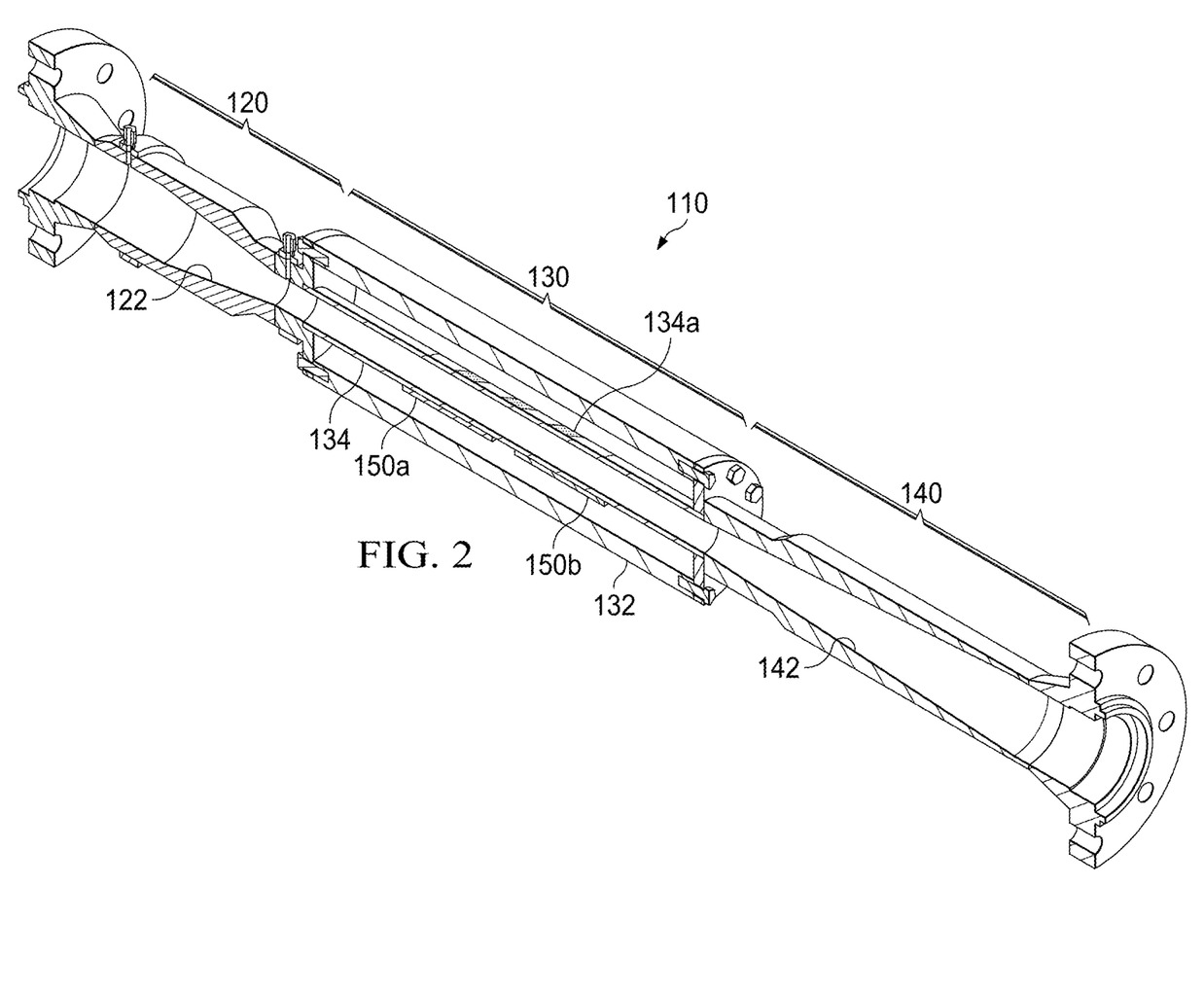
FIG. 2 illustrates a side cross-sectional view of an example multiphase flow meter system combining an extended throat venturi with microwave resonators configured in one possible arrangement and configuration.

In a particular embodiment, such as that shown in FIG. 2, a side cross-sectional view of an example multiphase flow meter system 110 combining an extended throat venturi with microwave resonators is shown. FIG. 2. illustrates an example layout of the particular system 110 having a venturi convergence section 120, an extended throat section 130, and a venturi divergence section 140. In an embodiment, a pair of microwave resonance sensors 150a and 150b can also be configured around or in close proximity to the extended throat section 130. In an embodiment, an external metallic housing 132 can form an outer housing around the extended throat section 130. In the embodiment illustrated in FIG. 2, the venturi convergence section 120 includes a convergence conical tapered section 122 that connects to the extended throat section 130. Further, the venturi divergence section 140 includes a divergence conical tapered section 142 that extends from the extended throat section 130. In the embodiment illustrated in regard to FIG. 2, the inner portion of the extended throat section is shown configured with a Polyetheretherketone or "PEEK" tube 134 with a printed water cut sensor (shown as part 134a of the PEEK tube) forming at least a portion of the PEEK tube 134. In general a PEEK tube is Polyetheretherketone based tubing, though other materials, including other plastics and polymers, that have similar inert and non-conductive properties may be substituted if desired. In an embodiment, the edges of the PEEK tube can be machined so that they can slide into the metallic convergence and divergence sections of the meter. Typically, the metallic convergence and divergence sections of the meter that the PEEK tube can be configured to slide into will also be configured with o-rings to prevent leakage.

Figure 3:
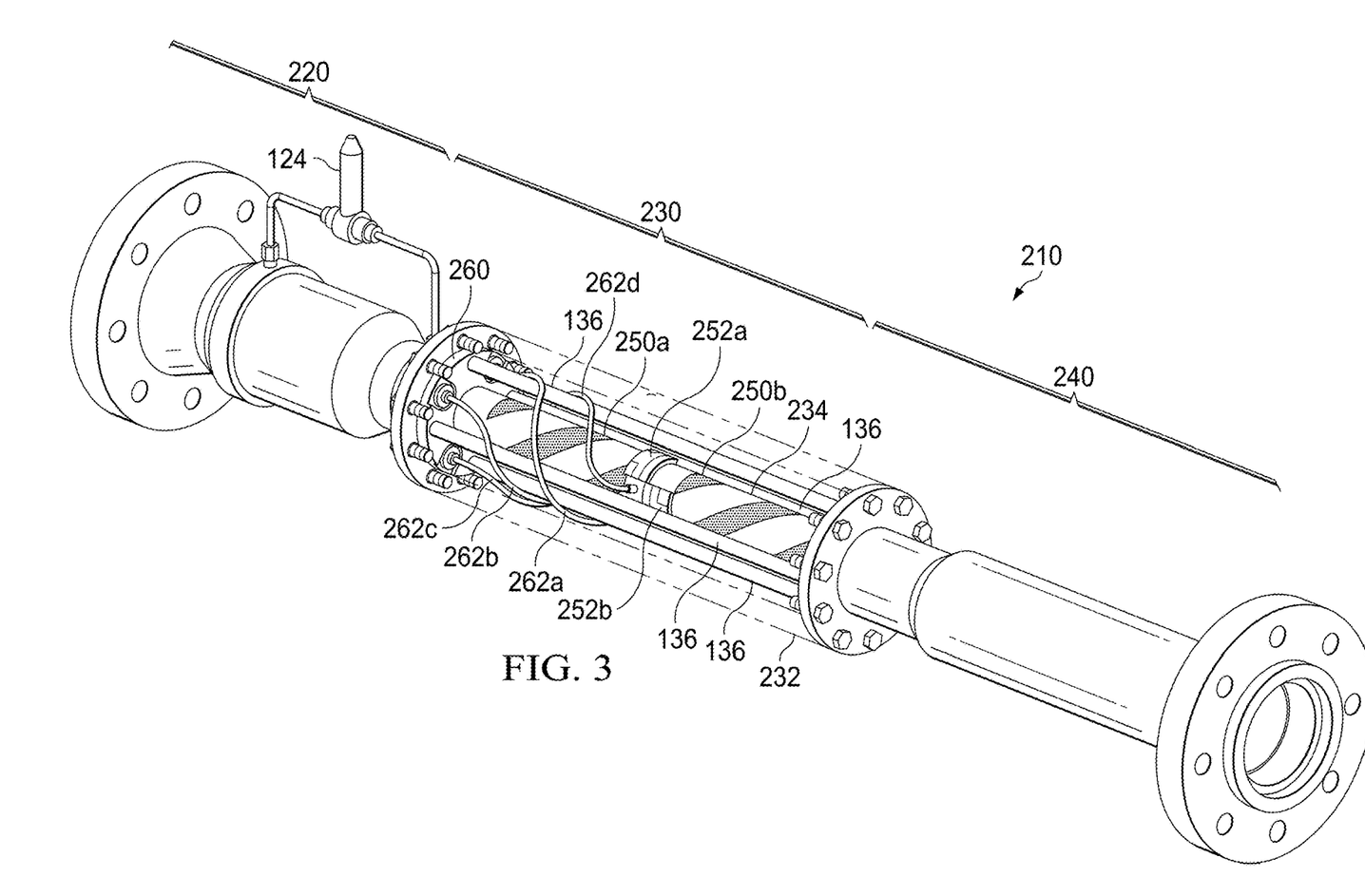
FIG. 3 illustrates a side perspective view of an example multiphase flow meter system combining an extended throat venturi with microwave resonators configured in one possible arrangement and configuration and including mutually orthogonal resonators.

Referring to FIG. 3, a perspective view of an example extended throat venturi multiphase flow meter system 210 combining an extended throat venturi with dual mutually orthogonal helical microwave resonators configured in one possible arrangement and configuration is shown. FIG. 3. illustrates an example layout of the particular system 210 having a venturi convergence section 220, an extended throat section 230, a venturi divergence section 240. In an embodiment, and as shown in the embodiment illustrated by FIG. 3, an external housing 232 can form an outer housing around the extended throat section 230. In an embodiment, a pair of dual mutually orthogonal helical microwave resonators 250a and 250b, which can be configured around the extended throat section 130. The dual mutually orthogonal helical microwave resonance sensors can be configured to be rotated to have substantially 90 degrees of rotational difference between their helixes, as is shown in FIG. 3. In an alternative embodiment, additional helical orthogonal microwave resonators can be configured beyond the two shown in FIG. 3. Additionally, in an embodiment and as shown in the example configuration of FIG. 3, non-metallic supporting rods 136 can be configured as part of the system 210 to support semi-precision co-axial radio frequency connector cables ("SMA cables") 262a, 262b, 262c, and 262d that extend from first and second microwave resonator feedlines 252a and 252b, respectively. In an embodiment, and as shown in FIG. 3, the SMA cables 262a, 262b, 262c, and 262d can be configured to extend from the feedlines 252a and 252b to a bulkhead plate 260 that receives the SMA cable connections. In an embodiment, a differential pressure transducer 124 can also be configured on the system 210 to take differential pressure measurements. In a particular embodiment and as illustrated and described with respect to FIG. 2 (not shown in the external housing views of FIG. 3), the venturi convergence section can be configured to include a convergence conical tapered section that connects to the extended throat section and the venturi divergence section can be configured to include a divergence conical tapered section that extends from the extended throat section. The sensor configuration of the embodiment described in relation to FIG. 3 allows for the measurement of the water-fraction in two phase oil-water flow irrespective of the flow regime. In the illustrated and described embodiment, the helical shaped microwave resonators 250 help rotate the electric fields ("E-fields") inside a PEEK tube 234 of the extended throat section 130 of the venturi. The rotating E-fields allows for the measurement of the fluid or multiphase mixture from all possible orientations in 360° span allowing for the described and illustrated extended throat venturi multiphase flow meter system 210 to be orientation insensitive.

In an embodiment, the E-fields of the microwave resonator not only exists inside the PEEK tube but can fringe outwards as well. In this context, fringe outwards means that some of the E-fields penetrate the air between PEEK tube and outer metal. However, the system has generally been configured such that most of the E-fields stay inside the PEEK tube where the fluid to be measured flows, depending on the desired configuration of the particular assembly. Presence of any material (especially metals) in the area between PEEK tube and the outer metallic cylinder may affect the E-field and the resonance operation of the sensors. Thus, to achieve an optimal and reliable system, it is desirable to minimize the amount of metallic materials in this space. Further, the presence of material in the area around the sensors can affect their performance. With this in mind, in an embodiment, the sensor configuration and placement can be optimized, taking the outer housing around the extended throat section into consideration. For example, in an embodiment, the distance between the outer housing and the sensors can be configured to be 1.7 inches, which has been determined to be an optimized separation distance of metal from the configured sensors, at least for the particular configuration shown with respect to FIG. 3. In an embodiment, this distance can be configured to be proportional to the outer diameter of the PEEK tube which, at least for the particular configuration shown with respect to FIG. 3, has been determined to be 2.15 inches. In an embodiment, and as shown and described in regarding to FIG. 3, the outer diameter of the PEEK tube can be configured to be 2.15 inches. In an alternate embodiment the diameter and length of the PEEK tube can be increased along with the separation distance to account for any increase in fringing fields based on the new PEEK tube dimensions.

In order to determine optimal configurations, a simulation of a resonator along with a complete housing structure in high frequency simulation software was performed. Since, in an embodiment, a resonator configuration may consist of two mutually orthogonal spiral resonators whose responses closely track each other, a simulation was performed with just one resonator to facilitate faster simulation completion time. Similarly, the area of the simulation housing section was restricted to the venturi throat portion so that simulation time could be reduced. Since the other configured sensor would typically have a similar response and, in a particular configuration, the resonance frequency of two sensors will be averaged out to achieve high accuracy, the high frequency simulation software model with just one resonator is substantially accurate.

Figure 4:
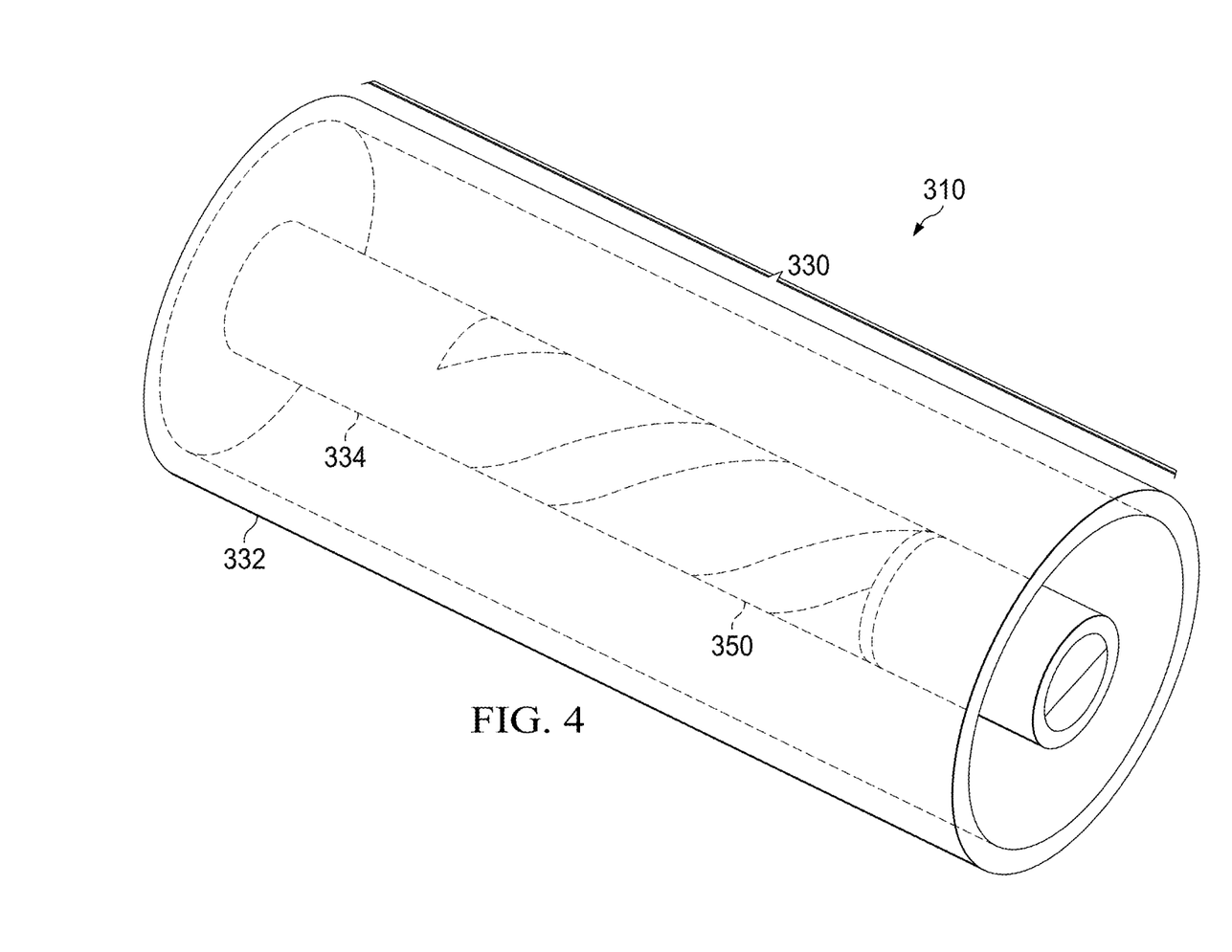
FIG. 4 illustrates a illustrates a cut-away side perspective view of an example multiphase flow meter system combining an extended throat venturi configured in one possible arrangement and configuration and including a single spiral based resonator sensor.

FIG. 4 illustrates the portion of the high frequency simulation software model that was simulated. FIG. 4 shows an enlarged perspective view of an example extended throat venturi portion of a multiphase flow meter system 310. FIG. 4. illustrates just a portion of the particular system 310, and what is shown is an extended throat section 330 with only a single orthogonal microwave resonator 350 surrounding a centrally located PEEK tube 334. The extended throat section 330 also includes a metallic external housing 332.

The model shown in FIG. 4 was simulated for different fractions of water and oil (0% to 100% with a step size of 10%) put inside a 7 millimeters ("mm") thick PEEK tube surrounded by a stainless steel metallic enclosure having an inner dimension (diameter) of 140 mm and an outer dimension of 167 mm and composed of stainless steel (SS-316). The resonator's response based on the simulations performed are shown in FIG. 5.

Referring to FIG. 5, the graphic illustrated shows that the sensor may be quite sensitive to the change in water fraction in oil. For example, for this embodiment, for the full range change of 0% to 100% water fraction in oil, the resonance frequency changes from 186.1 megahertz ("MHz") to 126.1 MHz which is a percentage shift of almost 47.6%. The percentage frequency shift depends upon the ratio of changing medium to the fixed medium. For a particular configuration, a shift of 47.6% is sufficient to achieve the desired water cut measurement resolution using sophisticated readout circuitry or VNA. In an embodiment, one example readout circuitry configuration can include a microwave oscillator connected to a pair of sensor resonators. In an embodiment, the oscillator can consist of an unstable transistor and some RLC (Resistor/Inductor/Capacitor) components. In an alternative embodiment, a VNA or vector network analyzer can be configured which is an off-the-shelf test instrument manufactured by a variety of different companies. A VNA can come configured in different form factors ranging from table-top to pocket-sized VNA. Generally, a VNA has complicated microwave circuitry inside to perform S-parameter measurements, such as the example S-parameter measurements shown in FIG. 5. Of note, other configurations will also provide full range water fraction in oil measurements, and a particular system can be configured to match various criteria such as size, dimension, or material, and other requirements that may be preferred for a particular systems function.

Referring again to FIG. 5, another observation is that, for this particular configuration and simulation, the resonator gives sharp resonance dips (below −30 dB for all mediums) indicating high quality factor of the resonator. High quality factor can help in pin pointing the resonance frequency of the sensor resulting in high resolution and accuracy of the sensor.

In a particular embodiment, such as that shown in FIG. 3, extended throat venturi multiphase flow meter systems can be configured with a computer system to perform analysis of measurement data. Such a computer system can be configured with a computer circuit board comprising a processor, I/O (input/output) channels, memory, a network interface, and non-volatile memory with loaded software (collectively "the computer system"). The software can include an operating system, communications interface program, and a microwave resonance control and monitoring program. In an alternative embodiment these programs may be combined or run on the bare system without an operating system.

Figure 6:
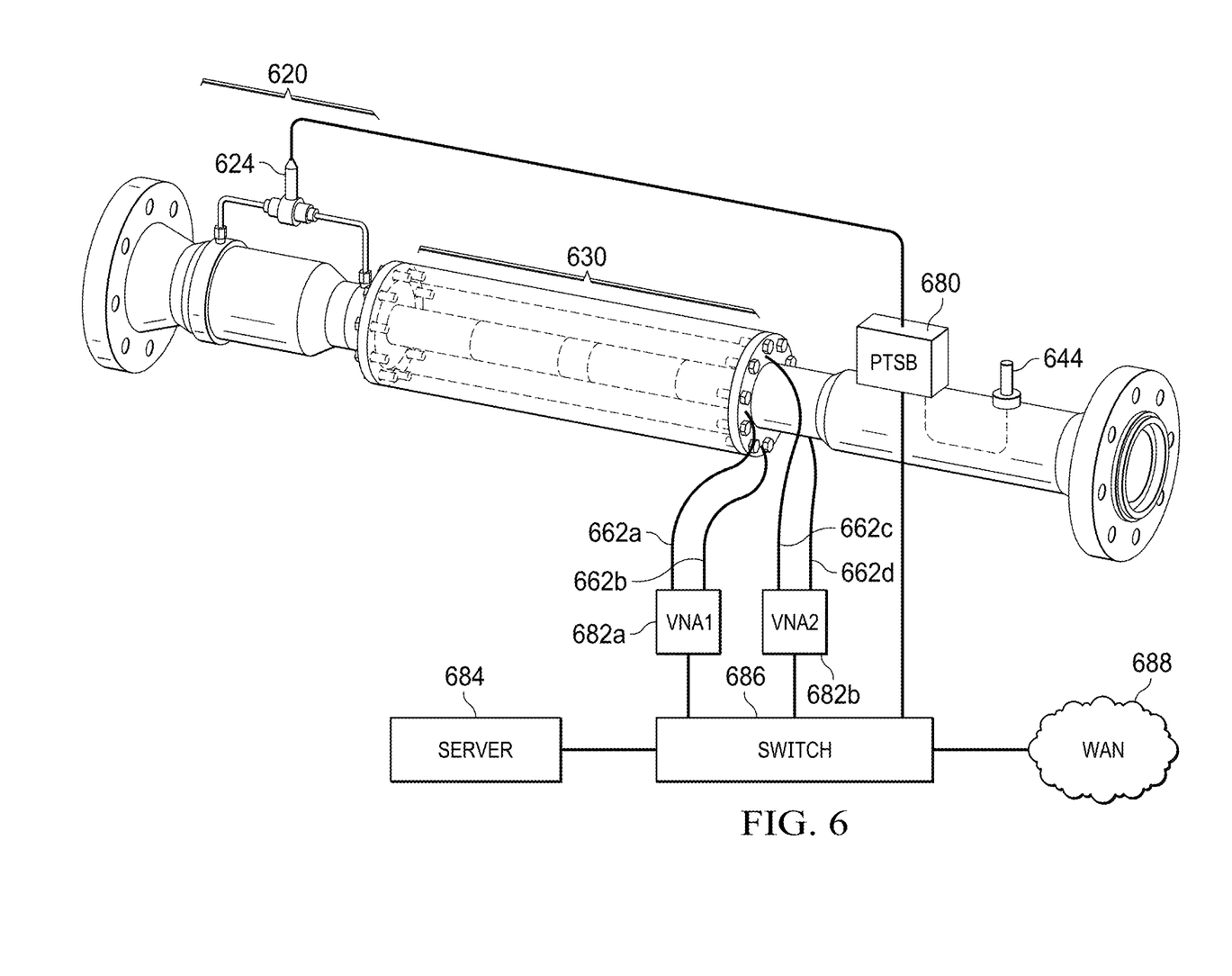
FIG. 6 illustrates a side perspective view of an example multiphase flow meter system combining an extended throat venturi with microwave resonators configured in one possible arrangement and configuration.

Referring to FIG. 6, an example multiphase flow meter system is shown. This system can be configured similarly to other embodiments described. The example shown in FIG. 6 is configured with a venturi convergence section 620, a dual microwave resonator section 630, and further includes SMA to external VNA connection cables 662a, 662b, 662c, and 662d. A pair of cables is connected to each resonator internally and then to a particular VNA such that the S-measurements can be determined. As shown, VNA connection cables 662a and 662b connect to VNA1 682a and VNA connection cables 662c and 662d connect to VNA2 682b. In an embodiment each VNA configured can connect to an Ethernet switch 686, though other similar communications equipment can be configured. For example, it may be desirable to configure wireless communications equipment as part of the VNA or other equipment in a particular system. The Ethernet switch 686 can further be configured to connect to a wide area network or WAN 688 and to a server 684. Alternatively other computing systems such as a laptop or micro-computer can be configured as part of this system in place of the server or multiple computing devices may be configured. Further, in an embodiment, and as shown in FIG. 6, a differential pressure transducer 624 can be configured as well as a temperature transducer 644. A pressure/temperature sensor box or PTSB 680 may also be configured to communicate measurements from the differential pressure transducer 624 and temperature transducer 644 over Ethernet to the switch 686. These measurements can then be communicated to configured computing systems such as server 684 or over the wide area network or WAN 688 for additional processing, logging, or display to an end user.

In addition to the described configurations and systems, software can be configured on a server, laptop, or other similar computing system, such as an Arduino, that can interpret sensor data from any configured VNA devices and PTSB devices over Ethernet or other communications interfaces that may be configured. This sensor data can be processed and the parameters of interest can be displayed on a display terminal. Alternatively, this data can be stored or logged for later use. For example, the data may be communicated to and stored in the cloud or other systems that would allow remote use and viewing of the data. The data can also displayed to an end user in graphical form such that water cut and flow rate information can be observed or the data can be averaged over a particular time period. Various display options can be configured based on what may be desired for a particular system.

From the description provided above, numerous different embodiments including embodiments that include software are envisioned that can be combined with general purpose hardware. A computer system can be created with various components to carry out the methods of the various embodiments including a non-transitory computer readable medium that can contain instructions for a software program to implement the method of the embodiments.

The above disclosure is meant to be illustrative of the various embodiments that are described. Various modifications will become apparent to those skilled in the art once the disclosure is considered as a whole.

The invention claimed is:

1. An extended throat venturi multiphase flow meter system, comprising:
   a venturi convergence section;
   an extended venturi throat section connected to the venturi convergence section and further comprising:
      an outer metallic housing,
      a polymer tube centrally located within the outer metallic housing,
      dual microwave resonance sensors configured within the outer metallic housing and further positioned on the polymer tube such that measurements can be taken of multiphase flows within the polymer tube, and
   a venturi divergence section connected to the extended venturi throat section;
   the dual microwave resonance sensors of the extended venturi throat section further configured to communicate with a computer system, the computer system further comprising:
      a computer circuit board,
      a microprocessor configured on the computer circuit board, the microprocessor configured with input/output channels,
      memory configured to be in communication with the microprocessor,
      a data bus extending between the memory and the microprocessor, and
      a network interface configured to be in communication with the microprocessor,
      non-volatile memory configured to be in communication with the microprocessor, and
      a software program stored on the nonvolatile memory that enables the microprocessor to collect and process the sensor measurement data.

2. The extended throat venturi multiphase flow meter system of claim 1, wherein the dual microwave resonance sensors are mutually orthogonal helical microwave resonance sensors.

3. The extended throat venturi multiphase flow meter system of claim 2, wherein the mutually orthogonal microwave resonance sensors are configured to collect measurement data and communicate it to the computer system.

4. The extended throat venturi multiphase flow meter system of claim 3, wherein the computer system has a stored simulated data set over a range that allows for the correlation of microwave resonance sensor readings to 0-100% water cut values and wherein the software program of the computer system is configured to correlate a particular resonance sensor measurement to a particular water cut percentage value.

5. The extended throat venturi multiphase flow meter system of claim 4, wherein the computer system software program is further configured to collect microwave resonance sensor measurement values over a given time period such that they can be averaged and 0-100% water cut value look ups can be determined for the averaged value, thereby reducing processing overhead based on correlation table look ups of the computer system.

6. The extended throat venturi multiphase flow meter system of claim 2, wherein the wherein the dual microwave resonance sensors of the extended venturi throat section are further configured with feedlines attached to each resonance sensor to communicate the resonance sensor measurements.

7. The extended throat venturi multiphase flow meter system of claim 2, wherein the dual mutually orthogonal helical microwave resonance sensors are rotated to have substantially 90 degrees of rotational difference between their helixes.

8. The extended throat venturi multiphase flow meter system of claim 1, wherein the venturi convergence section is further configured with a differential pressure transducer.

9. The extended throat venturi multiphase flow meter system of claim 1, wherein the venturi divergence section is further configured with a temperature transducer.

10. A method of analyzing sensor data using an extended throat venturi multiphase flow meter system, comprising the following steps:
   deploying an extended throat venturi multiphase flow meter system at a wellsite, the extended throat venturi multiphase flow meter system comprising:
      a venturi convergence section;
      an extended venturi throat section connected to the venturi convergence section and further comprising:
         an outer metallic housing,
         a polymer tube centrally located within the outer metallic housing,
         dual microwave resonance sensors configured within the outer metallic housing and further positioned on the polymer tube such that measurements can be taken of multiphase flows within the polymer tube, and
      a venturi divergence section connected to the extended venturi throat section;
      the dual microwave resonance sensors of the extended venturi throat section further configured to communicate with a computer system, the computer system further comprising:
         a computer circuit board,
         a microprocessor configured on the computer circuit board, the microprocessor configured with input/output channels,
         memory configured to be in communication with the microprocessor,
         a data bus extending between the memory and the microprocessor,
         a network interface configured to be in communication with the microprocessor, non-volatile memory configured to be in communication with the microprocessor, and a software program stored on the nonvolatile memory that enables the microprocessor to process the sensor measurement data, the method further comprising the step of:

collecting and logging, by the computer, system, microwave resonance sensor measurement values for processing and analysis.

11. The method of claim 10, wherein the dual microwave resonance sensors are mutually orthogonal helical microwave resonance sensors.

12. The method of claim 11, wherein the dual mutually orthogonal microwave resonance sensors are configured to collect measurement data and communicate it to the computer system.

13. The method of claim 12, wherein the computer system has a stored simulated data set over a range that allows for the correlation of microwave resonance sensor readings to 0-100% water cut values and wherein the software program of the computer system is configured to correlate a particular resonance sensor measurement to a particular water cut percentage value.

14. The method of claim 13, wherein the computer system software program is further configured to collect microwave resonance sensor measurement values over a given time period such that they can be averaged and 0-100% water cut value look ups can be determined for the averaged value thereby reducing processing overhead based on correlation table look ups of the computer system.

15. The method of claim 10, wherein the wherein the dual microwave resonance sensors of the extended venturi throat section are further configured with feedlines attached to each resonance sensor to communicate the resonance sensor measurements.

16. The method of claim 11, wherein the dual mutually orthogonal helical microwave resonance sensors are rotated to have substantially 90 degrees of rotational difference between their helixes.

17. The method of claim 10, wherein the venturi convergence section is further configured with a differential pressure transducer.

18. The method of claim 10, wherein the venturi divergence section is further configured with a temperature transducer.

* * * * *